United States Patent [19]
DiVita et al.

[11] Patent Number: 4,929,837
[45] Date of Patent: May 29, 1990

[54] METHOD FOR DETECTING PINHOLES AND INCOMPLETE COVERAGE OF HERMETIC COATINGS ON OPTICAL FIBER WAVEGUIDES

[75] Inventors: Sam DiVita, West Long Branch, N.J.; Howard E. Rast, Jr., Solana Beach, Calif.

[73] Assignee: The United States of America as represented by the Secretary of the Navy, Washington, D.C.

[21] Appl. No.: 29,125

[22] Filed: Mar. 23, 1987

[51] Int. Cl.$^5$ .................... G01N 21/64; G01N 21/88
[52] U.S. Cl. ................... 250/461.1; 250/302; 356/73.1
[58] Field of Search ............ 250/461.1, 302; 350/96.29; 65/3.11; 356/73.1

[56] References Cited

U.S. PATENT DOCUMENTS

| | | | |
|---|---|---|---|
| 3,808,434 | 4/1974 | Gutbier | 250/302 |
| 4,049,413 | 9/1977 | French | 350/96.29 |
| 4,292,341 | 9/1981 | Marcuse et al. | 65/3.11 |
| 4,317,996 | 3/1982 | Davis | 250/302 |
| 4,362,943 | 12/1982 | Presby | 250/461.1 |
| 4,473,599 | 9/1984 | Elion | 350/96.29 |
| 4,536,654 | 8/1985 | Vaerman | 250/461.1 |
| 4,621,193 | 11/1986 | Van Hoye | 250/461.1 |
| 4,630,890 | 12/1986 | Ashkin et al. | 65/3.11 |
| 4,675,728 | 6/1987 | Egger et al. | 250/461.1 |

Primary Examiner—Janice A. Howell
Assistant Examiner—William F. Rauchholz
Attorney, Agent, or Firm—Harvey Fendelman; Thomas G. Keough

[57] ABSTRACT

A method detects incomplete coverage of hermetic coatings applied to optical fibers during in-line optical fiber fabrication procedures as well as off-line applications. A fluorescent material surrounds the core region of the optical fiber prior to the formation of the hermetic coating on the optical fiber and energy is radiated in the optical fiber to propagate in the cladding mode. This causes an excitation of the fluorescent material to fluoresce in response to the propagated energy. An appropriately disposed detector detects levels of emitted fluorescence along the length of the optical fiber to indicate where the hermetic coating is incomplete or where pinholes in the hermetic coating are located. Optionally, the fluorescent material is located outside of the cladding layer, inside of the cladding layer near its outer surface or throughout the cladding region to fluoresce when excited by the propagated energy. Different wavelengths of radiation can be used which excite different fluorescent materials so that pinholes or incomplete coating coverage can be detected in hermetic coatings that have different chemical compositions.

13 Claims, 5 Drawing Sheets

FIG. 1

PRIOR ART

METHOD FOR DETECTING PINHOLES AND INCOMPLETE COVERAGE OF HERMETIC COATINGS ON OPTICAL FIBER WAVEGUIDES

STATEMENT OF GOVERNMENT INTEREST

The invention described herein may be manufactured and used by or for the Government of the United States of America for governmental purposes without the payment of any roylaties thereon or therefor.

BACKGROUND OF THE INVENTION

Stress corrosion is a phenomenon which leads to strength degradation in optical fibers under stress. Hydrogen and water present in the environment are principle agents which combine with stress to accelerate slow crack growth in vitreous materials. Hermetically coated optical fibers have evolved to prevent stress corrosion since this is particularly detrimental to the use of fibers in adverse environments. These hermetic coatings have been applied by several methods to assure a continuous complete covering of fibers to prolong their useful life. Ideally, from the manufacturinig view point, hermetic coatings should be deposited on-line as the preform is being fiberized as it is drawn from a furnace or after the fiber is drawn while it is still hot from the furnace. On-line deposition of the hermetic coating is more economical than off-line and is compatible with subsequent in-line overcoating by polymeric materials to form a buffer layer to further protect the fiber from abrasion and permit handling of the fiber for cabling etc.

One known method of forming a hermetic coating on a fiber relies on the depositon of metals from a liquid melt or by vaporization, sputtering, or plasma ion deposition techniques. Dielectric materials such as SiN, SiON, SiC, SiOC, SnO or other metal oxides also have been deposited by chemical vapor deposition, sputtering, or RF and plasma ion depostion. Good results are obtained if the coatings are maintained in a thin region, from 100-500 A thick; this thickness has been found to provide good adhesion with mechanical and thermal compatibility with the optical fiber.

Because these films or coatings are so thin, however, it is difficult to determine the quality of the coverage, detect pinholes or areas of incomplete coverage and to detect and quantify such defects, except through indirect, inferential techniques which have been unacceptable for some high reliability applications.

Methods to detect "pinholes", include Scanning Electron Microscopy (SEM), immersion in hydrofluoric acid solutions, and dynamic fatique measurements. The SEM method requires the observation of the surface in an electron mciroscope. Clearly, this is a very slow, time consuming and expensive procedure. Practically speaking, it can only be applied to examine very small lengths of fiber. The technique of immersing samples in hydrofluoric solution relies on the highly corrosive action of hydrofluoric acid on silica materials. In a given concentration of hydrofluoric solution, silica materials and fibers rapidly dissolve. If the fiber is coated with a hermetic material resistant to attack, the dissolution is significantly reduced in rate. The rate of dissolution, however, depends on the presence or absence of pinholes, or, stated more precisely, on the density and area of defects exposed to the acid solution. Unfortunately, this technique does not directly quantify or identify the location and degree of coating of non-coverage.

Dynamic fatique measurements are made by subjecting fibers to varying rates of tensile stress. Under low rates of stress, uncoated fibers will exhibit low average strengths indicative of crack formation and growths to critical intensities. At higher rates of tensile stress application, the average strengths are higher, indicating the reduction of static fatique which is a rate limiting process. In fact, at very high rates, the average strengths are indentical to the strengths measured in the absence of water. On the other hand, a truly hermetic coating without pinholes should exhibit the same fatique behavior and average strength of measurements performed in the absence of water. This technique, again, does not quantify the density and areas of non-coverage, but only suggests that coverage is not complete.

Thus there is continuing need in the state-of-the-art for a method of detecting imcomplete coverage of and pinholes in a hermetic coating on an optical fiber which lends itself to in-line fiber fabrication procedures as well as off-line applications.

SUMMARY OF THE INVENTION

The present invention is directed to providing a method for detecting incomplete coverage of and pinholes in a hermetic coating to an optical fiber. A fluorescent materical is provided about the core region of the optical fiber prior to the formation of the hermetic coating on the optical fiber. Energy is radiated through the optical fiber to propagate in the cladding modes and result in the excitation of the fluorescent material to fluoresce. The hermetically coated optical fiber is passed by an appropriate detector for detecting levels of emitted fluorescence along the length of the optical fiber to indicate where hermetic coating is incomplete and where pinholes in the hermetic coating are located. The fluorescent material can be located throughout the cladding or near its outer surface or outside and adjacent the outer surface of the fiber cladding prior to the application of the hermetic coating. In either location the fluorescent material fluoresces so that the detector can provide indications as to incomplete coverage or pinholes in the hermetic coating. Selection of the proper fluorescent material to fluoresce at the proper wavelengths is made so that different hermetic clatings having different transmissive properties may be monitored (for example some hermetic coatings may be transparent, partially transmissive or opaque to particular fluorescent wavelengths). Proper selection assures that the appropriate detectors will properly indicate incomplete coverage or pinholes in the hermetic coatings.

An object of the invention is to provide for detecting incomplete coverage of a hermetic coating or pinholes in a hermetic coating that is applied to an optical fiber.

Still yet another object of the invention is to provide for a method of detecting imcomplete coverage of and pinholes in a hermetic coating on an optical fiber that is rapid and nondestructive to the optical fiber.

Stll yet a further object of the invention is to provide a method of detecting incomplete coverage of and pinholes in a hermetic coating that lends itself to a quantitative measurement along the lengths of a hermetically coated optical fiber.

Yet another object is to provide for an improved method for determining completeness of a hermetic coating on an optical fiber that lends itself to in-line fabrication techniques as well as off-line applications.

Another object of the invention is to provide for a method of determining an incomplete hermetic coating or pinholes therein on an optical fiber that has fluorescent materials formed in association with fiber cladding.

Still another object is to provide for a method of detecting incomplete coverage of and pinholes in a hermetic coating on an optical fiber that incorporates selective fluorescent materials that fluoresce at discrete wavelengths so as to provide a responsive indication of incomplete coverage of one hermetic coating or another that have different chemical compositions.

Still another object is to provide for propagating radiation in the cladding mode to excite fluorescent materials associated with the cladding of an optical fiber to assure detection of the fluorescence where incomplete coverage or pinholes occur in a hermetic coating on the optical fiber.

Still another object of the invention is to provide for a method of detecting incomplete coverage of or pinholes in a hermetic coating that lends itself to an in-line fiber fabrication process that uses the furnace radiation to provide cladding mode propagation for the excitation of fluorescent materials associated with the cladding.

These and other objects of the invention will become more readily apparent from the ensuing specification and claims when taken in conjunction with the attached drawings.

DESCRIPTION OF THE PREFERRED EMBODIMENT

Figure 1:
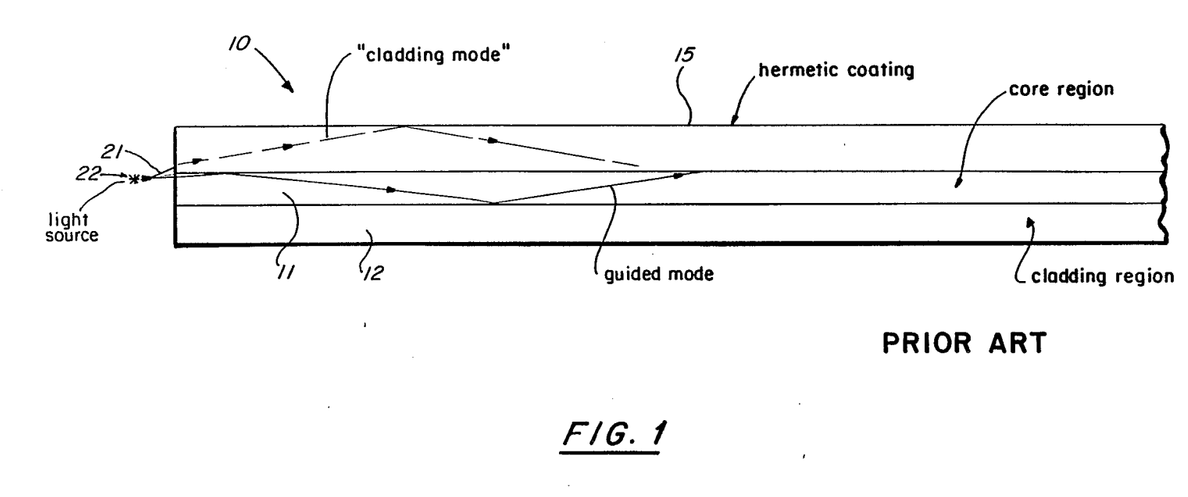
FIG. 1 is a not to scale showing of a state-of-the-art optical fiber waveguide having a hopefully complete hermetic coating, propagating energy in the cladding mode in the cladding regions as well as propagating energy in the guided mode in the core region.

Referring now to FIG. 1 of the drawings a typical optical fiber 10 having a core region II and cladding region 12 is provided with a hermetic coating 15 that hopefully makes the fiber more attractive for some applications where the problems associated with stress corrosion are to be reduced. Such a hermetically coated fiber may not, however, provide designers with the desired resistance to the effects of hydrogen and water if there is an incomplete coverage of, or pinholes in the hermetic coating.

Figure 2A:
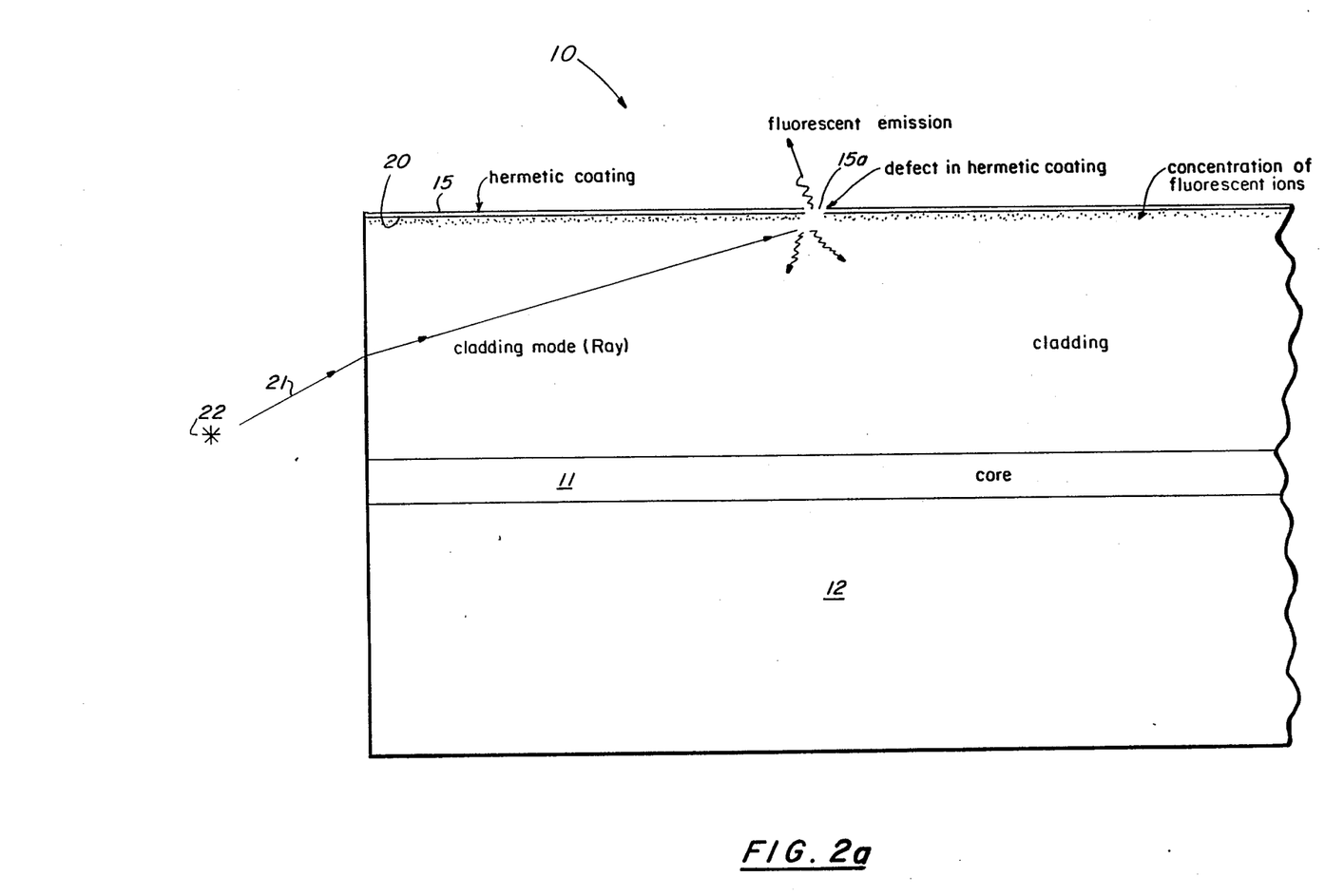
FIG. 2a shows an exploded view, not to scale, of an optical fiber waveguide in which the propagated energy in the cladding modes creates a fluorescent emission from fluorescent materials associated with the volume near the surface of the cladding regions.

This inventive concept avoids such a contingency by assuring a positive indication of incomplete coverage. Fluorescent materials 20, see FIG. 2a are provided in association with the cladding region and have the property of fluorescing when stimulated by electromagnetic energy of the proper wavelength. Light 21 coming from a light source 22 is launched into fiber 10 to propagate in the so-called "cladding modes" which can, depending on the material and loss mechanisms, propagate a considerable distance along the length of the fiber before the light is totally attenuated. Energy launched into the core region is transmitted in guided modes and does not, to an appreciable degree, find its way into the cladding region because of its "reflection" at the boundary between the two regions which have different indices of refraction.

Impurity ions forming the fluorescent material are introduced into the cladding region as shown in FIG. 2a next to the outer surface of the cladding region on which the hermetic coating is applied. The impurity ions absorb photons from the higher order cladding modes and reemit fluorescence photons in an angle of $4\pi$ sterradians. In other words, the "cladding modes" are bound by the cladding-air interface since the index of the cladding is greater than air and waveguiding results. Upon absorption of the light by impurity centers, the fluorescence is emitted in all directions, including perpendicular to the waveguide axis, wherein it is no longer confined, but becomes visible to an observer.

When the fiber is overcoated with a hermetic coating 15 having pinholes 15a, see FIG. 2a, this perpendicular emission becomes detectable at this point. Another undesirable condition in the hermetic coating occurs when the thickness or completeness of the coating varies from being completely opaque to being partially transparent to the fluorescence emission excited as described. This area of incomplete coverage will appear as spots of different contrast than the completely covered areas and, thus, are detected, enumerated, and measured when appropriate means are provided. It has been found that this process of detecting pinholes or incomplete coverage lends itself to automation and can be made on-line with the fiber drawing process or is performed in a off-line application as will be elaborated on below.

As a prerequisite to locating pinholes or incomplete coverage the fluorescent materials must be appropriately associated with the cladding region of the optical fiber. Several methods are available to incorporate fluorescent materials, ions, in the cladding region.

A first method relies on diffusion. In the Chemical Vapor Depositon (CVD) or Modified Chemical Vapor Deposition (MCVD) processes of preparing preforms to be drawn into fibers from a furnace, a pure silica tube is rotated in a lathe while a burner traverses the length of the tube. Gases of the appropriate composition flow through the tube, oxidize, and deposit metal oxides, such as $GeO_2$, $Al_2O_3$, $Na_2O$, or other oxides such as $B_2O$ and $P_2O_5$. The tube is subsequently collapsed under heating to form a solid vitreous rod, otherwise known as a preform, having a multicomponent glass concentration in the center. The center region has an index higher than the outer layers, thereby, producing waveguiding of light when the rod is fibererized.

In the diffusion process proposed herein, the rod is further subjected to the application of a vapor or solution of fluorescent ions which diffuse into the outer layer or "cladding" portion of the preform. This is effected by suspending the preform in a solution or heated vapor of the appropriate fluorescence ionic material for a proper duration and with correct concentration to permit passage of the ions into the outer layer. Diffusion takes place when a material, pressure, or temperature gradient exists. The process for performing this diffusion is established in the art and will not be elaborated on in great detail here. An optical fiber 10 is drawn and has a layer of fluorescent ions inside the outer surface of cladding region 12, note FIG. 2a. The point is that a sufficiently high concentration of fluorescent ions is built up inside the outer surface of the cladding region to enable observation of the emitted fluorescence when "cladding mode" radiating energy is propagated through the cladding region to excite the fluorescent ions by this exciting wavelength which could be ultraviolet, infrared, or the like.

In the diffusion process, the amount of material dQ diffusing in a time dt, across a plane of area A perpendicular to the area, is:

$$dQ = -DA \frac{\partial \mu}{\partial x} dt$$

where the $\partial \mu / \partial \chi$ is the concentration gradient and D is the diffusion coefficient The solution of this equation depends on several conditions and the geometry of the process, but is the approach to predict the conditions of achieving the correct concentration of fluorescent ions and the process parameters. The distribution of impurity ion concentration will decrease, generally, in an exponential dependence with distance from the surface of the outer layers. Thus, it will be greatest on the surface which is the desired result.

Another method of introducing the fluorescent ions into an association with the cladding of the optical fiber calls for the insertion of a preform into a thin glass tube. This glass tube is made of a vitreous material containing rare earth or transition metal ions. Such glass tubes are commercially available and are known in the trade as didymium glass (DG). DG glasses are brightly fluorescent under UV excitation. The thin tube is collapsed onto the preform. When the fiber drawn in the usual way fluorescence ions 20b are carried in a layer 20' on the outside of the cladding region, see FIG. 2b.

Figure 2B:
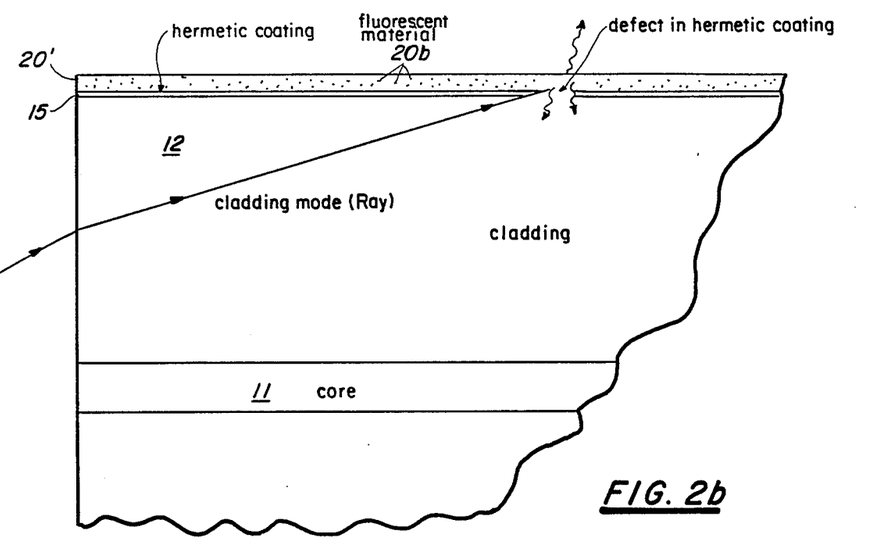
FIG. 2b shows a part of the FIG. 2a waveguide with a fluorescent material layer on the outside of the cladding region.

The tube-over-rod method will contain a more uniformly constant concentration of impurity ions 20b throughout the thickness of tube-layer 20'. However, since the ions are not within the "cladding" or core regions, no deleterious losses occur by its presence. In the case where the fluorescent ions are distributed throughout the cladding region, losses may occur because guided modes have evanescent extension into the cladding region, but this will be inconsequential provided the impurity ions do not absorb at the wavelength of signal transmission.

Other techniques may be relied upon to coat the fiber with fluorescent ions, layer them on the outside of the fiber, or introduce the ions into the cladding prior to when the fiber is drawn from the preform or as the fiber is being drawn prior to the application of the hermetic coating. It was once thought to be important to limit concentration of the fluorescent ions to the outer part of the cladding region as in FIG. 2a in order not to degrade the optical transmission of the fiber. However, more recent investigations have revealed that the fluorescent ions 20 c can be disposed throughout the cladding region more or less uniformly, see FIG. 2c, to gain the novel advantageous of this method without seriouly degrading the optical transmission characteristics of the core region. The incorporation of the fluorescent ions can be performed during the preform fabrication stage by suitably mixing in the proper material in the molten cladding portion of the preform, for example.

Having an optical fiber 10 with fluorescent ions 20a, 20b or 20c associated with its cladding layer allows the determination of the completeness of a hermetic coating 15. Applying fluorescent ions to a fiber after it has been drawn or incorporating them into the outer layer of the preform before the fiber is drawn from a furnace, permits a hermetic coating 15 to be added "on-line" while the fiber is still hot.

After this operation has been performed, the observation or detection of fiber coverage by the hermetic coating can be made immediately in an "on-line" continuation or may be deferred to a later time for an "off-line" testing at a laboratory or work site. In either case, the principles of this method are identical, except that an "on-line" observation and detection may be preferable since the heat and light of the furnace maybe used to stimulate fluorescence of a particular fluorescent material. In a later "off-line" process a separate light source and coupling arrangement might be needed to introduce "cladding mode" exciation for the fluorescent ions.

Figures 3A, 3B:
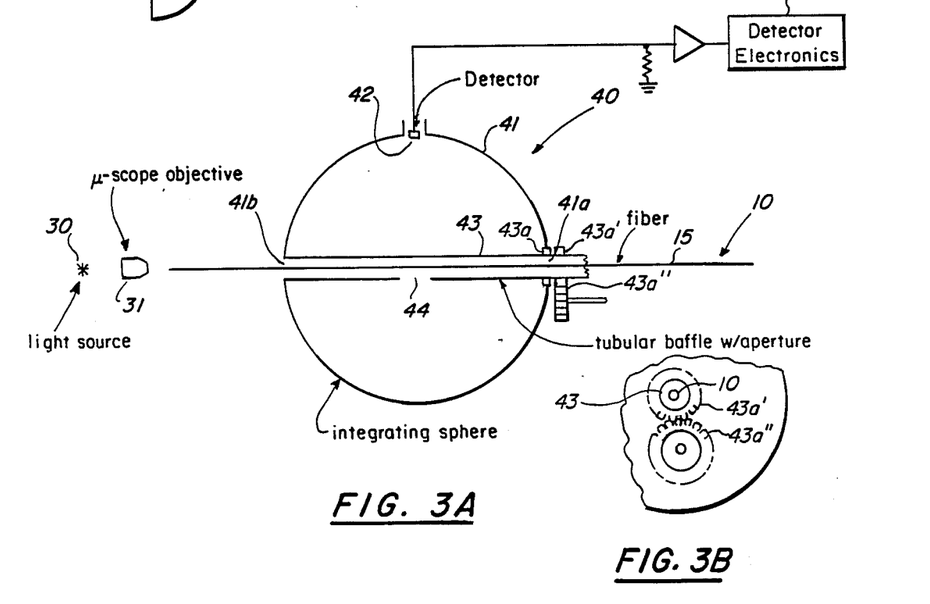
FIGS. 3a and 3b shows one embodiment of a detector used with the method of this invention to enable both in-line and off-line examination of a hermetically coated optical fiber and a typical rotation mechanism, respectively.

A typical detection apparatus 40 for enabling the detection of areas of incomplete coverage or pinholes is shown schematically in FIG. 3a. An optical fiber 10 is suitably disposed with respect to a light souce 30 that is provided with a suitable objective lens 31, for example a microscope objective lens to assure that light, possibly ultraviolet light, excites the fiber in the "cladding" modes of propagation. As mentioned earlier, if, an"in-line" application is desired, the light source could be the furnace associated with the fiber drawing operation to transmit energy including infrared, to propagate in the "cladding" mode.

Providing the cladding modes of radiated energy are not rapidly attenuated before they reach detection apparatus 40, they are absorbed by fluorescent impurity ions in the outer surface of the fiber which will fluoresce or re-emit as fluorescence photons at right angles to the fiber axis. Any areas of incomplete coverage of the hermetic coating 15 become apparent because of their contrast with the covered area. Such contrast is facilitated by the detection apparatus 40 which has an intergrating sphere 41 with a highly reflective inner surface. This is used to collect light that is transmitted from pinholes or incompletely covered areas of the hermetic coating. A detector 42 senses the light that is transmitted through pinholes or incompleted areas of coverage and provides a responsive signal for appropriate interconnected monitoring circuitry 42a.

Fiber 10 passes through apertures 41a and 41b provided in the integrating sphere and tranverses the length of a tubular baffle 43. The tubular baffle is rotated in a bearing 43a at an appropriate speed by a ring gear 43a' and pinion mechanism 43a", see FIG, 3b, such that an aperture 44 in the baffle exposes the complete length of the fiber during its passage through the tubular baffle. The interior of the tubular baffle, optionally, is blackened to absorb any light in directions away from aperture 42. Light exiting the aperture is reflected by the highly reflective inner surface of the sphere, to be collected and monitored via detector 42. The size of the aperture can be varied to correspond to the resolution and density of defects to be observed in the hermetic coating. To observe hermetic covering defects on the fiber, the tube is rotated at a predetermined rate, while the fiber is advanced through the tube at a rate which is appropriate to expose the entire hermetic coating to the aperture. The mechanism for accomplishing this can be done continuously or stepwise, but, in any case, the power incident at the detector is measured and recorded as a function of position along the fiber's length. If the fiber draw speed is $s=dl/dt=1$ and the slit aperture has a length d, then the tube must be rotated at anangular velocity $w=2\pi l/d$ to ensure that any defects on the surface of the fiber have been exposed during its transit through the sphere.

Figure 4:
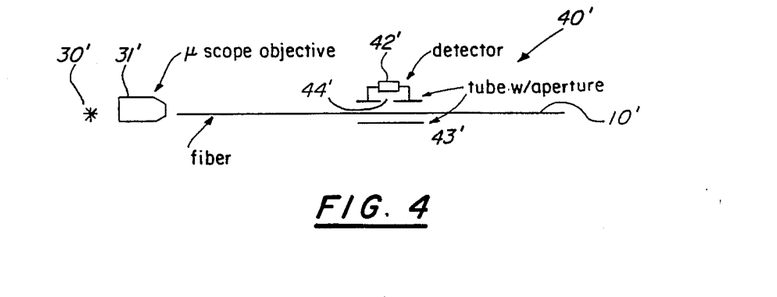
FIG. 4 shows a variation of the detector for both in-line and off-line detection applications.

A variation in the construction of the detector apparatus is shown in FIG. 4. A fiber 10' is advanced through a rotating tube 43' having an aperture 44'. Detector 42' is mounted on the rotating tube, to rotate therewith and the responsive signals are drawn off by a slip ring assembly, not shown. Obviously, the sensitivity of this detector is different from that depicted with respect to the embodiment of FIG. 3a; however, such component selections are routinely made by one skilled in the art to which this invention pertains.

Other, more sophisticated, arrangements are possible, such as using multiple detectors around the perimeter of the fiber and having the fiber drawn through the peripherally disposed detector assembly. Another arrangement on might use would be threshold detector arrays that discriminate against transmitted fluorescence through areas of complete coverage, such that signals that exceed this magnitude are detected as areas of incomplete coverage or pinholes.

A preferred arrangement of detectors and threshold sensors, however, depends on the type and transparency of the hermetic coating. Obviously, metal hermetic coatings, are opaque to visible light except in the presence of pinholes. Other hermetic coatings might be completely transparent to fluorescence at some wavelength or may provide an insufficient contrast to observe pinholes or incomplete coverage. These sort of design problems are overcome by selecting fluorescent materials or ions whose wavelength of emission is absorbed by a particular hermetic coating in a discernable, detectable degree, so that areas of incomplete coverage and pinholes are detectable by the arrangement referred to above. In this regard, certain materials and ions which fluoresce in the infrared spectrum, such as $Er^{3+}$, $Tm^+$, $Nd^{3+}$, $Ti^{3+}$, $Cr^{3+}$, $Yb^{3+}$, $Co^{2+}$, $V^{2+}$, or $Ni^{2+}$ may be selected or other fluorescent materials may be chosen to allow readings at a suitably responsive detector arrangement for the determination of areas of incomplete coverage or pinholes in the hermetic coating. The listed materials are set forth as examples and are not intended to be exhaustive.

The method described above, provides for the quantitative measurement of pinholes along the surface of a hoped-for hermetically coated fiber. Use of the fluorescent ion-doped material associated with the region allows the observation of defects in the hermetic coating. The observation of these defects is attributed to the fluorescing ions when excited by cladding modes of suitable wavelengths of radiation. A variety of detector-sensitivity-responsiveness options are open for the designer when the type of hermetic coating and its transmission characteristics are known. That is, if a particular hermetic coating is opaque to some wavelengths of energy, irrespective or the amount of coating on the fiber, wavelengths will not penetrate to show increased transmissivity with thinner or incomplete covering. When this is the case, a designer will select the appropriate fluorescing material which exhibits emissions at the wavelengths which will provide an indication of increased transmission through areas of incomplete coverage.

One of the limitations in using UV radiation in the cladding mode of propagation, is that this energy is not transmitted great distances in fibers that have been designed to be optimized at the commerical transmission wavelengths of light, namely $0.85\mu m$, $1.3\mu m$, and $1.55\mu m$ and the air-glass interface, although providing some waveguiding, is not optimized for minimum transmission losses. However, UV fluorescent materials and radiation can be used to implement an off-line quality control (QC) of a hermetically coated fiber. As a quality control method, pieces are sampled of a manufactured production run. QC statistical methods are applied to quantify the population of areas of insufficient coverage and pinholes.

This measuring techinque is also useful as analytical tool as new hermetic coating processes are developed or as different hermetic coatings are created. This disclosed procedure can give designers a real time evaluation of the effectiveness of the new process or material, to assure optimization in minimal time.

For example, when a new hermetic coating process is to be investigated, only a pure didymium glass rod need be formed into a preform from which r fibers are drawn prior to being hermetically coated. This material of course is not a good waveguide, but would provide designers with a means for detecting pinholes in the hermetic coating process or limitations in the possibly new hermetic coatings themselves.

As an option to diffusing the fluorescent materials in the cladding region, a designer could use CVD deposition. A deposition 20d of a rare earth or transition metal oxides or other compounds can be made over the outer surface of the cladding region of the preform or the pure optical fiber prior to hermetic coating. The deposited material 20d', would have the same fluorescent effect and avoids the manufacturing complications of the diffusion or tube-over-rod process to simplify the detection of pinholes and incomplete coverage of the hermetic coating, see FIG. 2d.

Figure 2C:
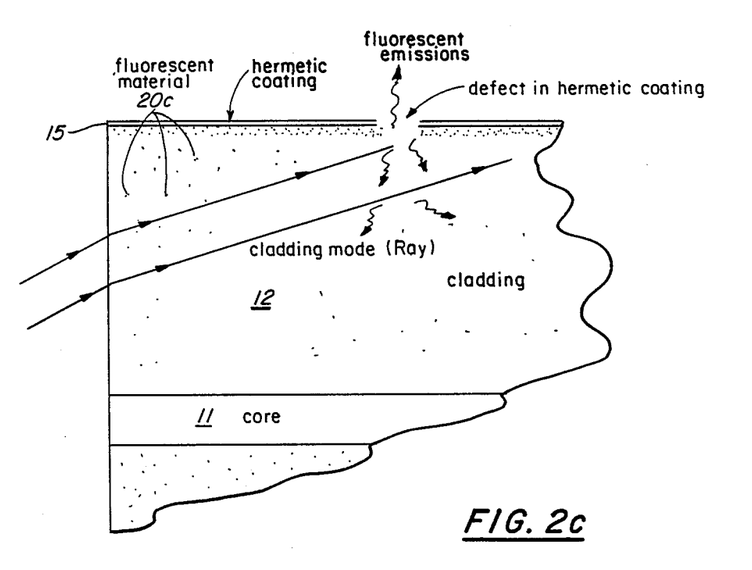
FIG. 2c depicts a part of the FIG. 2a waveguide showing fluorescent material throughout the cladding region emitting fluorescent emission.
Figure 2D:
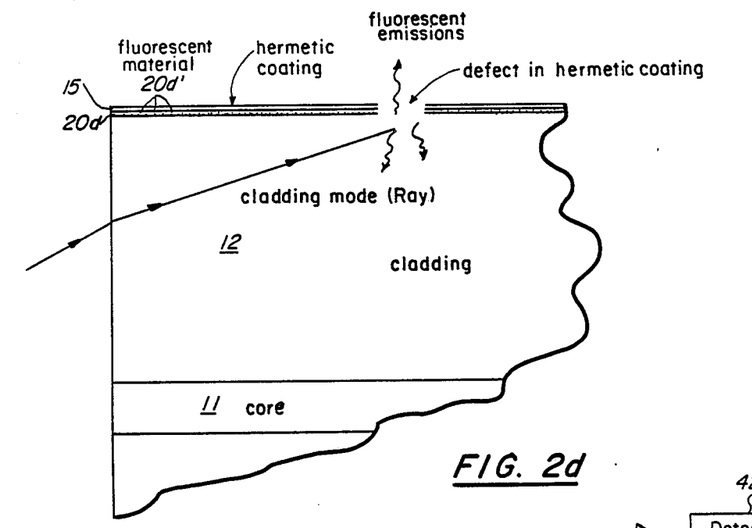
FIG. 2d shows the fluorescent material deposited on the outer surface of the cladding region.

The fluorescent ions optionally are dissolved or diffused in glasses to effect the same result using other well-known fiber fabrication techniques such as: The Double Crucible Method, Vapor Axial Deposition (VAD), Outside Vapor Deposition (OVD), and all other variants of these methods to assure that the fluorescent material is distributed in the cladding region as the fiber is being drawn. The cladding region will appear as shown in FIG. 2c.

Figure 5:
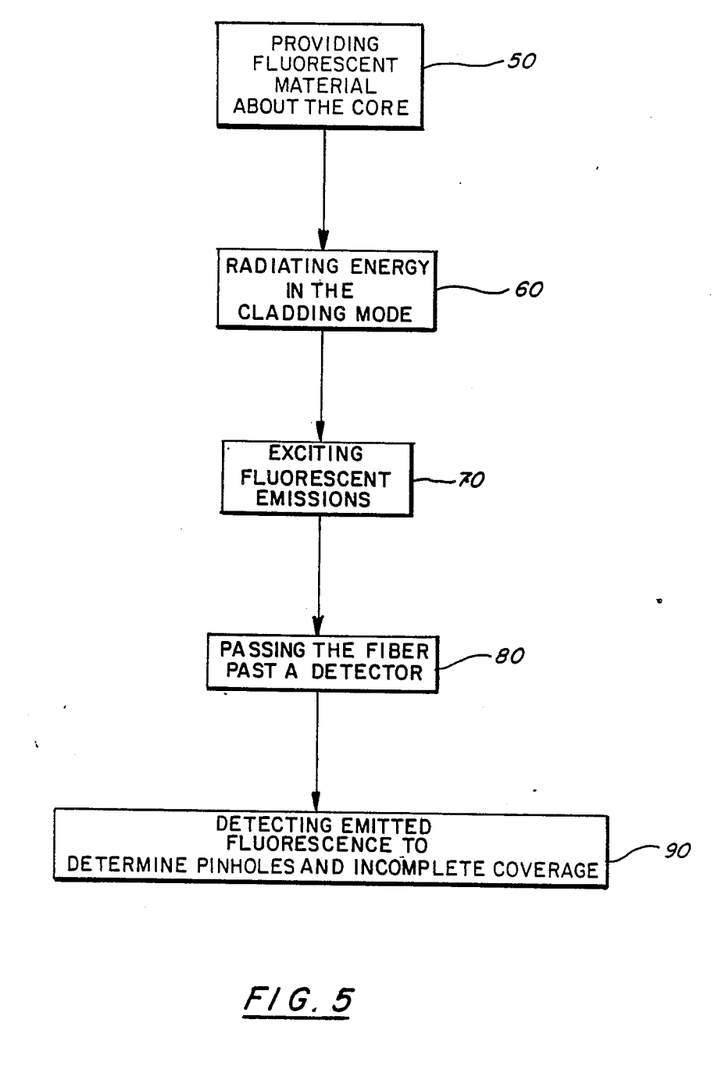
FIG. 5 depicts the method of determining incomplete coverage of and pinholes in a hermetic coating on an optical fiber.

Looking to FIG. 5, the method of the invention of detecting incomplete coverage of and pinholes in a hermetic coating on an optical fiber calls for the providing 50 of a fluorescent material about the core region of an optical fiber prior to the formation of a hermetic coating on the optical fiber. Radiating 60 energy through the optical fiber after the hermetic coating has been applied to propagate in the cladding modes causes the exciting 70 of fluorescent emissions from the fluorescent material. During the passing 80 of the optical fiber through a detector apparatus, a detecting 90 of levels of emitted fluorescence occurs along the length of the fiber where the hermetic coating is incomplete or where pinholes in the hermetic coating are located.

Obviously, many modifications and variations of the present invention are possible in the light of the above teachings. It is therefore to be understood that within the scope of the appended claims the invention may be practiced otherwise than as specifically described.

We claim:

1. A method of detecting incomplete coverage of and pinholes in a hermetic coating on an optical fiber having a core region and cladding region comprising:
   providing a fluorescent material surrounding the core region of the optical fiber prior to the formation of the hermetic coating on the optical fiber;
   radiating energy in the optical fiber having the hermetic coating to propagate in a cladding mode;
   exciting the fluorescent material to fluoresce in response to the energy propagated in the cladding mode;
   passing the optical fiber having the hermetic coating past a detector of fluorescence; and
   detecting levels of emitted fluorescence by the detector along the length of the optical fiber to indicate where the hermetic coating is incomplete and where pinholes in the hermetic coating are located.

2. A method according to claim 1 in which the step of providing a fluorescent material is the providing of a layer of fluorescent ions surrounding the core region, the step of radiating energy is the radiating of UV energy in the cladding mode, the step of exciting is the exciting of the fluorescent ions to fluoresce and the step of detecting is the detecting of levels of fluorescence to indicate where the hermetic coating is incomplete.

3. A method according to claim 2 in which the step of providing a fluorescent material is the diffusion of fluorescent ions into an appropriate part of a preform that will correspond to the cladding region when the optical fiber is drawn.

4. A method according to claim 1 in which the step of providing a fluorescent material is the diffusion of fluorescent ions into an appropiate part of a preform that will correspond to the cladding region when the optical fiber is drawn.

5. A method according to claim 2 in which the step of providing a fluorescent material is the collapsing of a thin rod of vitreous material containing a fluorescent material onto a preform prior to drawing the optical fiber therefrom.

6. A method according to claim 1 in which the step of providing a fluorescent material if the collapsing of a thin rod of vitreous material containing a fluorescent material on a preform prior to drawing the optical fiber thereform.

7. A method according to claim 2 in which the step of providing is the diffusing of fluorescent ions throughout an appropriate part of a preform that will correspong to the outer part of the cladding region when the optical fiber is drawn.

8. A method according to claim 1 in which the step of providing is the diffusing of fluorescent ions throughout an appropriate part of a preform that will correspond to the outer part of the cladding region when the optical fiber is drawn.

9. A method according to claim 2 in which the step of providing is the depositing, as by chemical vapor deposition for example, of a fluorescent material coating on the outer surface of the cladding region of the optical fiber prior to its having a hermetic coating.

10. A method according to claim 1 in which the step of providing is the depositing, as by chemical vapor deposition for example, of a fluorescent material coating on the outer surface of the cladding region of the optical fiber prior to its having a hermetic coating.

11. A method according to claim 2 in which the step of providing is the dissolving and mixing of a fluorescent material in a preform part which forms the cladding region when an optical fiber is fabricated.

12. A method according to claim 1 in which the step of providing is the dissolving and mixing of a fluorescent material in a preform part which forms cladding region when an optical fiber is fabricated.

13. A method of detecting the coverage of a hermetic coating over a member having light transmissive properties comprising:
   providing a fluorescent material in the member;
   exciting the fluorescent material to emit fluorescence in response to energy radiated in a cladding mode; and
   detectiing levels of emitted fluorescence along the length of the member to indicate where the hermetic coating is incomplete and where the hermetic coating has pinholes.

* * * * *